United States Patent [19]

Mori et al.

[11] Patent Number: 5,457,396

[45] Date of Patent: Oct. 10, 1995

[54] ELECTRODE STRUCTURE OF METALLIC PARTICLE DETECTING SENSOR

[75] Inventors: Akira Mori; Ikuo Uchino; Atsuhiko Hirosawa; Kunihiro Yamasaki, all of Hiratsuka, Japan

[73] Assignee: Kabushiki Kaisha Komatsu Seisakusho, Tokyo, Japan

[21] Appl. No.: 119,067

[22] PCT Filed: Mar. 24, 1992

[86] PCT No.: PCT/JP92/00356

§ 371 Date: Sep. 14, 1993

§ 102(e) Date: Sep. 14, 1993

[87] PCT Pub. No.: WO92/17772

PCT Pub. Date: Oct. 15, 1992

[30] Foreign Application Priority Data

Mar. 27, 1991 [JP] Japan ..................... 3-085832

[51] Int. Cl.⁶ .................................... G01N 27/06
[52] U.S. Cl. .................... 324/724; 324/71.4; 324/698; 340/631
[58] Field of Search ..................... 324/693, 698, 324/710, 713, 715, 717, 722, 725, 71.1, 71.4, 204; 73/61.42; 377/12; 340/627, 631

[56] References Cited

U.S. PATENT DOCUMENTS

| | | | |
|---|---|---|---|
| 2,252,222 | 8/1941 | Van Os | 324/71.4 X |
| 2,349,992 | 5/1944 | Schrader | 324/698 |
| 3,233,173 | 2/1966 | Lees et al. | 324/71.4 |
| 3,422,417 | 1/1969 | Lowe | 340/631 |
| 4,030,028 | 6/1977 | Allender | 340/631 X |
| 4,070,660 | 1/1978 | Tauber . | |
| 4,127,808 | 11/1978 | Sproul et al. . | |
| 4,873,482 | 10/1989 | Gray | 324/71.4 |

FOREIGN PATENT DOCUMENTS

| | | | |
|---|---|---|---|
| 0186746 | 9/1985 | Japan | 324/724 |
| 60-227159 | 11/1985 | Japan . | |
| 62-6149 | 1/1987 | Japan . | |

OTHER PUBLICATIONS

IBM Technical Disclosure Bulletin, vol. 26, No. 5, Oct., 1983, New York, USA, pp. 2606–2607, J. Harper et al, Particle Detector.

Primary Examiner—Kenneth A. Wieder
Assistant Examiner—Diep Do
Attorney, Agent, or Firm—Frishauf, Holtz, Goodman, Langer & Chick

[57] ABSTRACT

An electrode structure of a metallic particle detecting sensor capable of detecting with high efficiency metal powders floating in a wide range in an oil tank. The electrode structure is formed by opposing, on a substrate, a pair of electrodes (1, 2), formed of thin film metals of such as Ta, W, Pt, Cr, Au or the like, having combed (toothed) structures with their respective teeth being meshed or interdigitated with each other.

20 Claims, 3 Drawing Sheets

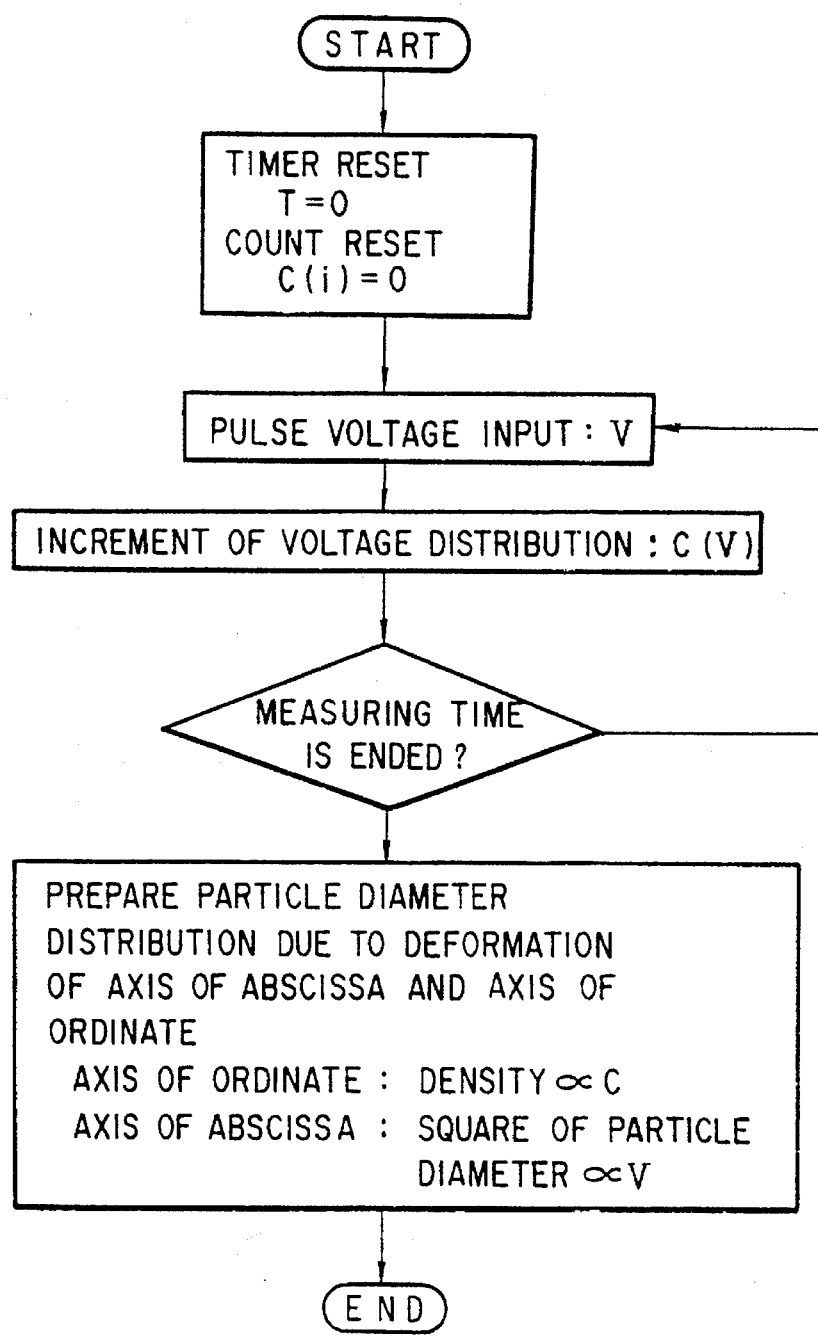

– 5,457,396 –

ELECTRODE STRUCTURE OF METALLIC PARTICLE DETECTING SENSOR

TECHNICAL FIELD OF THE INVENTION

This invention relates to an electrode structure of a sensor for detecting metallic particles mixed in a liquid such as lubrication oil.

BACKGROUND TECHNOLOGY OF THE INVENTION

Conventionally, as means for detecting presence or absence of metal powders floating in a lubrication oil, there is known means for detecting the mixing of the metal powders by adsorbing the metal powders by a magnet disposed, for example, on a bottom wall of an oil tank and detecting the change of magnetic flux at this time.

In the above conventional floating metal powder detecting means, the detecting means are disposed in a spot-like manner to the oil tank, and the detecting ability of one detecting means is limited. Accordingly, when it is required to perform the detection over a wide range, the provision of a large number of detecting means is inevitably required. The increasing of the location positions of the detecting means results in a problem of complicated detecting control thereof. Furthermore, in the above conventional detecting means, it is impossible to utilize the detecting means in a case where the metal powder is small in size and its mixed amount is relatively small such as several tens to several thousands PPM.

SUMMARY OF THE INVENTION

This invention was conceived in view of the above facts the object thereon is to provide an electrode structure of a metallic particle detecting sensor capable of detecting metal powders floating over a wide range of an oil tank, and detecting the metal powders with high efficiency even in a case where the metal powder is small in size and its mixed amount is relatively small.

To achieve the above object, the electrode structure of the metallic particle detecting sensor according to this invention has a structure wherein a pair of electrodes, each being formed of a thin film metal, is formed on an insulation substrate in a state that the electrodes are opposed to each other and have combed, interdigitated structures.

Furthermore, the electrodes are opposed with a distance (spacing) of 1 to 50 μm therebetween and each of said electrodes has a width 3 to 8 times of the opposing distance (spacing).

The thin film metal forming the electrodes may consists of a metal of Ta, W, Pt, Cr, Au or the like which does not constitute an insulator or semiconductor even when the thin film metal becomes an oxide.

In the electrode structure described above, when the metal powders exist between both of the electrodes with electric voltage of 30 - 50V being applied between the electrodes, a pulse voltage is generated between the end portions of the electrodes and this pulse voltage is detected.

According to this invention, since the metallic particle detecting sensor having a wide area in a plane can be manufactured, it is possible to detect the metal powders floating over a wide range of an oil tank and it is also possible to detect with high efficiency the floating metal powders even in a case where a small amount of the metal powders floats and its mixed amount is relatively small.

Furthermore, according to this invention, a mass production of the detection sensors can be done at once due to its structure and the combined detection of such as temperatures can be easily done. Furthermore, since the detection sensor can be formed so as to provide a curved surface, its application for the usage thereof can be widened. Still further, since the specific heat is small and the time up to the temperature balance is short, the follow-up characteristic to a temperature change of the lubrication oil is good and a stable detection result can be achieved in spite of a temperature change of the lubrication oil.

The above and other objects, modes and advantages of this invention will be made clear to those skilled in the art by the following description and explanation made with reference to the accompanying drawings showing concrete examples as embodiments in compliance with the principle of this invention.

BRIEF DESCRIPTION OF THE DRAWINGS

FIG. 5 is a flow chart showing a sequence of calculating a distribution of metallic particle diameters.

DETAILED DESCRIPTION OF PREFERRED EMBODIMENT

A preferred embodiment of this invention is described below with reference to the accompanying drawings.

Figure 1:
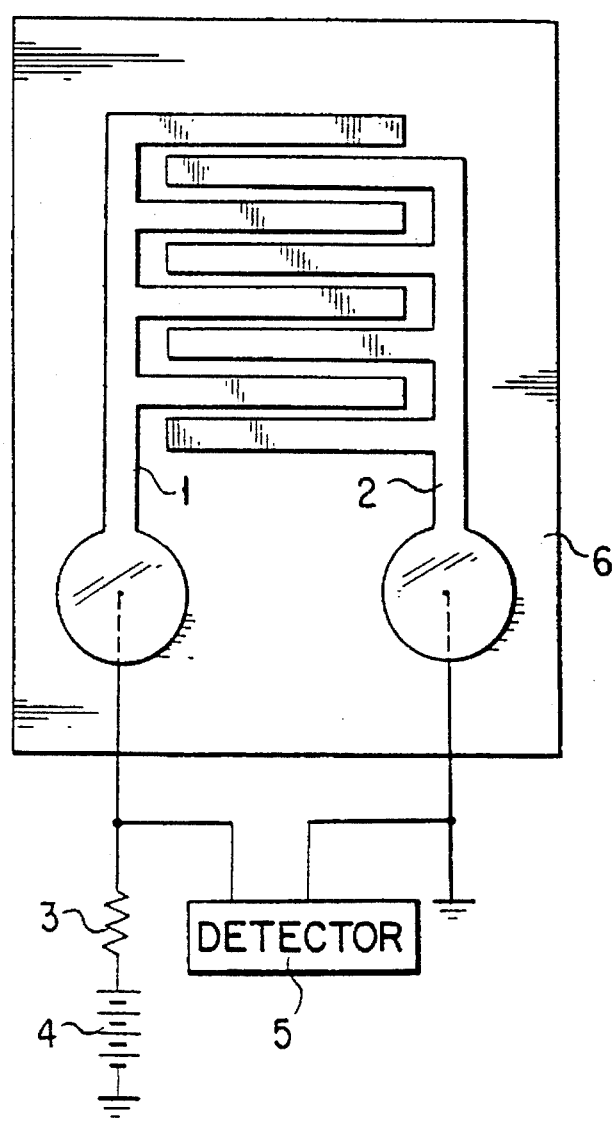
FIG. 1 is a schematic plan view showing one embodiment of this invention.

In the drawings, reference numeral 1 denotes an input electrode, and numeral 2 is an earth or grounded electrode. Both electrodes 1 and 2 have comb shapes with parallel teeth (see FIG. 1) and are opposed to each other so as to be interdigitated with each other (i.e., the parallel teeth mesh with each other as shown in FIG. 1). The opposing distance or spacing between the electrodes 1 and 2 is 1–50 μm. A current limiting resistor 3 and a power supply source 4 are connected to the input electrode 1. Reference numeral 5 denotes a detector.

Both of the electrodes 1 and 2 are formed in a shape of a thin film, on a substrate 6 having a good insulating property such as an alumina substrate or a sapphire substrate. These electrodes 1 and 2 are manufactured each by forming a thin film layer, on the substrate 6, having several thousands μm by a spattering or evaporation of a metal for the electrode and then effecting a laser trimming, lift-off, etching, or screen masking method, thus forming an assembled comb shaped structure.

A voltage of 30–50 V is applied between the electrodes 1 and 2, and a current limiting resistor 3 having a resistance of 5–20KΩ is utilized in series with power supply source 4. Further, it is not necessary to always use the current limiting resistor 3 in a case where the electrodes 1 and 2 have high electrode resistance.

Metal of Ta, W, Pt, Cr, Au or the like, which does not constitute an insulator or a semiconductor when such metal becomes an oxide, is utilized as the metal for the electrodes, and its electrical resistance is at least less than 10 KΩ.

The width of each of the electrodes 1 and 2 has an effect on the quantity of electricity through the electrodes. Namely, when the width is too small, the resistance becomes large and only a small current passes, resulting in that a polarization (electric filed) phenomenon hardly influences the metallic particles in the lubrication oil and the detection performance is hence made low. For this reason, it is preferred that the width of each of the electrodes 1 and 2 is 3–8 times of the opposing distance or spacing t (see FIG. 3) between the electrodes 1 and 2.

The metallic particle detecting sensor of the above structure is dipped in the lubrication oil and a voltage of 30–50 V is applied between the electrodes 1 and 2. According to the application of this voltage, in a case where the metal powders exist in the lubrication oil, a pulse voltage is generated between both ends of the electrodes 1 and 2, which is detected by the detector 5. This pulse voltage is generated at a time when small metal powders are tied (or arranged) in a row in the shape of a conductive bridge (see FIG. 3). The amplitude of this pulse voltage is in proportion to the square of the particle diameter and the frequency of the pulse generation is proportional to the particle density.

Accordingly, the particle diameter and the particle density of the metal powder in the lubrication oil can be found by detecting the pulse voltage and the pulse generating frequency by the detector 5.

Figure 2:
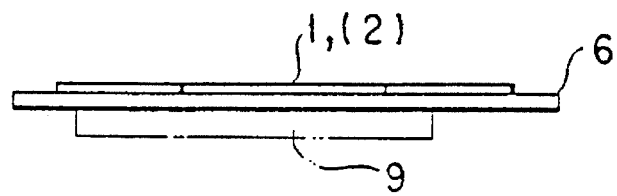
FIG. 2 is a schematic side view of the embodiment shown in FIG. 1.

Further, in the above embodiment, it is possible to bond a temperature detecting element 9 (FIG. 2) such as thermistor onto the back side surface of the substrate 6, thereby detecting the temperature as well as the metallic particles, thus achieving a combined detection.

Furthermore, since the specific heats of the electrodes 1 and 2 can be made small by constructing them so as to provide minutely fine structures, a time interval up to a time when the temperature of the electrodes 1 and 2 reaches the temperature of the lubrication oil can be made short, thus enabling the sensor to follow a temperature change of the lubrication oil.

Figure 3:
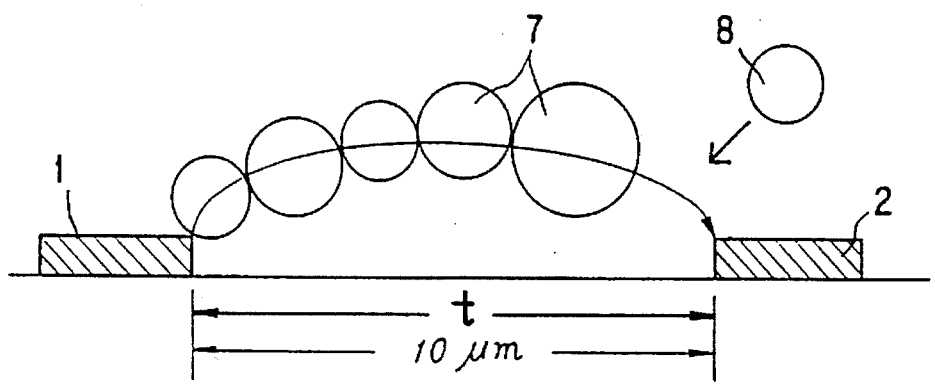
FIG. 3 is a modeled view showing a state in which metallic particles are tied in a row between two electrodes.

FIG. 3 is a modeled view showing the metallic particles in a condition of a tied or connected row between the electrodes 1 and 2, and shows that the polarization phenomenon (i.e., field created between electrodes 1 and 2 by the voltage applied between the electrodes) due to one electrode 1 acts on the metallic particles 7 floating in the lubrication oil and the metallic particles are successively connected in a tied row to the side of energized electrode 1. When another metallic particle 8 (FIG. 3) moves into a gap between the front or free end of the row of metallic particles 7 and the other electrode 2 (under the influence of the magnetic field produced by the energized electrodes) to thereby complete a conducting bridge therebetween, a pulse voltage is then generated between the electrodes 1 and 2 which is detected by the detector 5.

Figure 4:
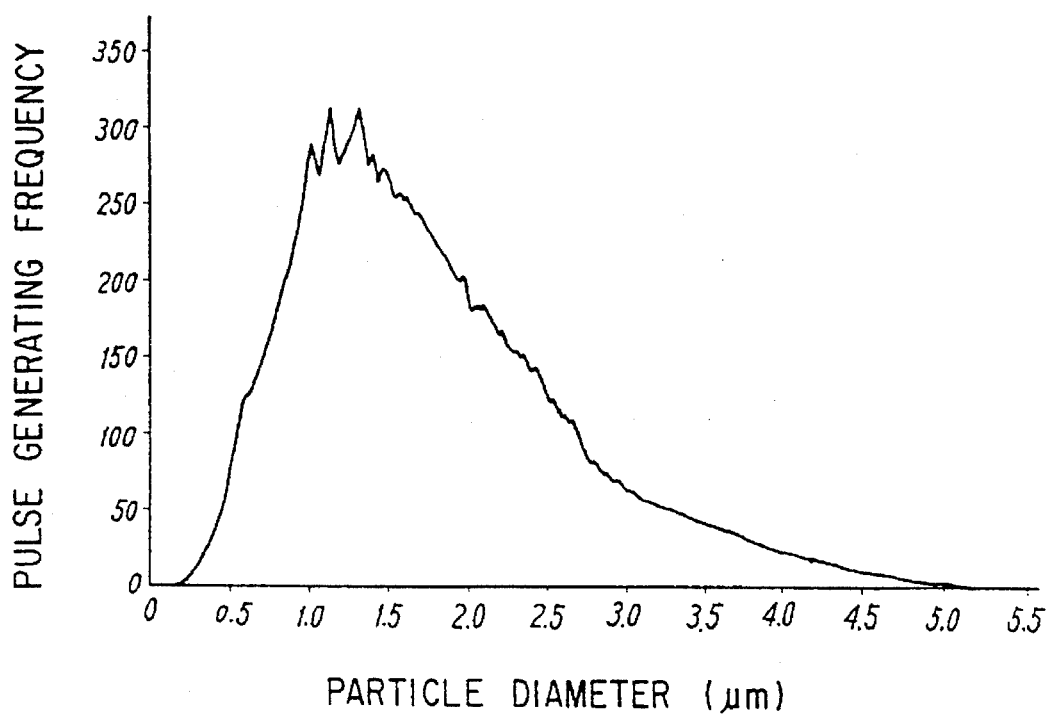
FIG. 4 is a relationship between the graph showing a particle diameter of a metallic particle in a lubrication oil and a pulse generating frequency.

FIG. 4 is a graph showing the relationship between the diameters of the metallic particles contained in the lubricating oil and the pulse generation frequency. In this detection, the distance t between the electrodes 1 and 2 was 10 μm and the applied voltage was 40 V. Further, the number of the pulses generated for 10 minutes were counted by the detectors as the pulse generating frequency. The particle diameters are a function of the amplitude of the pulse generation voltage.

From the above facts, by utilizing the graph shown in FIG. 4, the particle diameters are found by the pulse voltage at the detection working times, thereby detecting the density of the particles from the pulse generating frequency.

With reference to the flow chart of FIG. 5, a sequence for calculating a distribution of metallic particle diameters will be described.

First, a specific voltage level Vi (i=1, 2, 3, . . . ) and a pulse voltage measuring time T are decided and a timer is reset. Then, the pulse number (i.e., the number of pulses) having the voltage level Vi is integrated to obtain C(Vi). Next, in a time at which the measuring time of the timer does not reach the time T, the procedure for obtaining C(Vi) is repeated. When the measuring time reaches the time T, the measurement of the pulse voltage is stopped, and then, the particle density distribution of each of the metallic particles can be obtained by utilizing the fact that a square of the metallic particle diameter is proportional to the voltage Vi on the basis of the distribution of the pulse number C(Vi) of each of pulses of voltage level Vi and the fact that the density of the metallic particles having a diameter for generating a voltage pulse of the voltage level Vi is proportional to the value of C(Vi).

Another method for obtaining the distribution of the metallic particle diameters is as follows.

First, a specific voltage level Vi~Vi+ΔVi (i=1, 2, 3, . . . ) and the pulse voltage measuring time T are decided and the timer is then reset. Next, the pulse number (i.e., number of pulses) having the voltage level Vi~Vi+ΔVi is integrated to thereby obtain the value C(Vi). In a time at which the measuring time of the timer does not reach the time T, the procedure for obtaining C(ΔVi) is repeated. When the measuring time reaches the time T, the measurement of the pulse voltage is stopped, and then, the particle density distribution of each of the metallic particles is obtained by utilizing the fact that square of the metallic particle diameter is proportional to the value Vi on the basis of the distribution of the pulse number C(Vi) of each of voltage level Vi~Vi+ΔVi and the fact that a density of the metallic particles having a diameter Ri+ΔRi for generating a pulse voltage of the voltage level V1~Vi+ΔVi is proportional to the value C(Vi).

We claim:

1. An electrode structure of a metallic particle detecting sensor, for detecting electrically conductive metallic particles in a liquid, comprising:

an insulating substrate having a flat surface;

a pair of electrodes disposed on the flat surface of the insulating substrate, said electrodes being formed of respective thin metal films and being opposed to each other with a spacing therebetween, said electrodes each having a comb shape having a plurality of substantially parallel teeth, said substantially parallel teeth of the respective electrodes meshing with each other with said teeth of one electrode spaced from the teeth of the other electrode;

means for applying a voltage between the opposed electrodes to create an electric field between the opposed electrodes;

wherein metal particles in the liquid are influenced by the electric field created by the applied voltage to form a conductive bridge of the metal particles between the electrodes, which causes an electrical conduction between the electrodes, thus generating a pulse; and a detector for detecting the pulse voltage amplitude of the pulses generated between the opposed electrodes, wherein said detector determines the diameter and density of conductive metallic particles in the liquid as a function of at least the detected pulse voltage.

2. The electrode structure of claim 1, wherein said electrodes are opposed with a spacing of 1 to 50 μm therebetween, and wherein each of said electrodes has a width 3 to 8 times the spacing between the electrodes.

3. The electrode structure of claim 2, wherein the thin metal films forming said electrodes comprises a metal which does not constitute an insulator or semiconductor even when the thin metal films become an oxide.

4. The electrode structure of claim 3, wherein said metal is a metal selected from the group consisting of Ta, W, Pt, Cr and Au.

5. The electrode structure of claim 1, wherein the thin metal films forming said electrodes comprises a metal which does not constitute an insulator or semiconductor even when the thin metal films become an oxide.

6. The electrode structure of claim 5, wherein said metal is a metal selected from the group consisting of Ta, W, Pt, Cr and Au.

7. The electrode structure of claim 1, wherein said detector further detects a frequency of the pulses generated between said opposed electrodes.

8. The electrode structure of claim 1, wherein said voltage applying means applies a voltage of 30 to 50 volts between said opposed electrodes.

9. The electrode structure of claim 8, wherein said electrodes are opposed with a spacing of about 10 μm therebetween.

10. The electrode structure of claim 9, wherein said voltage applying means applies a voltage of about 40 volts between said opposed electrodes.

11. The electrode structure of claim 2, wherein said voltage applying means applies a voltage of 30 to 50 volts between said opposed electrodes.

12. The electrode structure of claim 11, wherein said electrodes are opposed with a spacing of about 10 μm therebetween.

13. The electrode structure of claim 12, wherein said voltage applying means applies a voltage of about 40 volts between said opposed electrodes.

14. The electrode structure of claim 3, wherein said voltage applying means applies a voltage of about 40 volts between said opposed electrodes.

15. The electrode structure of claim 14, wherein said voltage applying means applies a voltage of 30 to 50 volts between said opposed electrodes.

16. The electrode structure of claim 15, wherein said electrodes are opposed with a spacing of about 10 μm therebetween.

17. The electrode structure of claim 1, wherein said detector detects a number of pulses generated between said opposed electrodes in a predetermined time interval.

18. The electrode structure of claim 7, wherein a square of a diameter of the electrically conductive metallic particles causing the generation of the pulse voltage is proportional to the detected voltage, and a frequency of the pulses generated is proportional to a density of the conductive metallic particles which have a diameter in a predetermined range causing the generation of the pulse voltage.

19. A detector device for detecting metallic particles contained in a non-polar solvent, the detector device comprising a pair of comb-shaped electrodes which are disposed in the non-polar solvent, said comb-shaped electrodes having substantially parallel teeth which mesh with each other so that the teeth of one electrode are spaced from the teeth of the other electrode;

means for applying a high voltage between the comb-shaped electrodes; and means for measuring a pulse voltage generated by the high voltage applied between the comb-shaped electrodes due to the presence of said metallic particles in said non-polar solvent so as to measure a diameter and a density of the conductive metallic particles in the non-polar solvent.

20. A method of detecting electrically conductive metallic particles contained in a non-polar solvent, the method comprising:

arranging a pair of spaced apart electrodes in the non-polar solvent;

applying a voltage between the spaced apart electrodes; and measuring a diameter of conductive metallic particles in the non-polar solvent by measuring a pulse voltage generated at a time when the conductive metallic particles exist between the pair of spaced apart electrodes in the non-polar solvent; and wherein the pulse voltage generated in a predetermined time interval is calculated by every predetermined level and obtaining a particle diameter distribution based on a fact that a square of a diameter of conductive metallic particles causing the generation of the pulse voltage is proportional to the amplitude of the pulse voltage and a fact that a frequency of pulse voltage generation in the predetermined level is proportional to a density of the conductive metallic particles which have diameter in the predetermined range causing the generation of the pulse voltage in the predetermined level.

\* \* \* \* \*